(12) United States Patent
Sylvester et al.

(10) Patent No.: US 9,956,029 B2
(45) Date of Patent: May 1, 2018

(54) TELESCOPING DEVICE WITH SALINE IRRIGATION LINE

(71) Applicant: Medtronic Advanced Energy LLC, Minneapolis, MN (US)

(72) Inventors: Joseph Sylvester, Andover, MA (US); Himanshu K. Bhatt, Keller, TX (US); Tarquinio A. Bruno, Hampton, NH (US); Bhavesh D. Patel, Woburn, MA (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 436 days.

(21) Appl. No.: 14/688,723

(22) Filed: Apr. 16, 2015

(65) Prior Publication Data
US 2016/0120592 A1 May 5, 2016

Related U.S. Application Data

(60) Provisional application No. 62/073,705, filed on Oct. 31, 2014.

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 18/1402* (2013.01);
(Continued)

(58) Field of Classification Search
CPC .......... A61B 2017/00991; A61B 2018/00029; A61B 2018/00166; A61B 2018/00577;
(Continued)

(56) References Cited

U.S. PATENT DOCUMENTS

| 2,888,928 A | 6/1959 | Seiger |
| 3,682,130 A | 8/1972 | Jeffers |

(Continued)

FOREIGN PATENT DOCUMENTS

WO 2010113053 A1 10/2010

OTHER PUBLICATIONS

International Search Report and Written Opinion dated Dec. 2, 2015, for corresponding International Application No. PCT/US2015/050088; International Filing Date: Sep. 15, 2015 consisting of 10-pages.

*Primary Examiner* — Jaymi Della
(74) *Attorney, Agent, or Firm* — Christopher & Weisberg, P.A.

(57) ABSTRACT

An electrosurgical device includes a first shaft defining a proximal end, a distal end, and a lumen therethrough. A fluid delivery tube is disposed within the lumen, the fluid delivery tube defining a proximal end a distal end. An electrically conductive treatment element is in electrical communication with and coupled to the distal end of the first shaft, the electrically conductive treatment element includes a conductive fluid conduit in fluid communication with and affixed within a portion of the fluid delivery tube. A second shaft is in electrical communication with the first shaft, the first shaft being slideably disposed within the second shaft and movable from a first position in which the electrically conductive treatment element is proximate to the distal end of the second shaft to a second position in which the electrically conductive treatment element is advanced a distance away from the distal end of the second shaft.

19 Claims, 7 Drawing Sheets

(51) Int. Cl.
  *A61B 18/00* (2006.01)
  *A61B 17/00* (2006.01)
  *A61B 18/04* (2006.01)

(52) U.S. Cl.
  CPC ........ *A61B 18/148* (2013.01); *A61B 18/1477* (2013.01); *A61B 18/1482* (2013.01); *A61B 18/042* (2013.01); *A61B 2017/00991* (2013.01); *A61B 2018/00029* (2013.01); *A61B 2018/00166* (2013.01); *A61B 2018/00577* (2013.01); *A61B 2018/00589* (2013.01); *A61B 2018/00601* (2013.01); *A61B 2018/00607* (2013.01); *A61B 2018/1412* (2013.01); *A61B 2018/1472* (2013.01); *A61B 2217/007* (2013.01); *A61B 2218/002* (2013.01); *A61B 2218/007* (2013.01)

(58) Field of Classification Search
  CPC ........... A61B 2018/00589; A61B 2018/00601; A61B 2018/00607; A61B 2018/001412; A61B 2018/1472; A61B 2217/007; A61B 2218/002; A61B 2218/007; A61B 18/1477; A61B 18/14; A61B 18/148; A61B 18/1206; A61B 18/1402; A61B 18/042
  See application file for complete search history.

(56) References Cited

U.S. PATENT DOCUMENTS

| | | |
|---|---|---|
| 3,750,650 A | 8/1973 | Ruttgers |
| 3,907,339 A | 9/1975 | Stumpf et al. |
| 3,910,277 A | 10/1975 | Zimmer |
| 3,924,628 A | 12/1975 | Bingham et al. |
| 4,018,227 A | 4/1977 | Wallach |
| 4,022,215 A | 5/1977 | Benson |
| 4,060,088 A | 11/1977 | Morrison, Jr. et al. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,919,129 A | 4/1990 | Weber et al. |
| 4,931,047 A | 6/1990 | Broadwin et al. |
| 5,197,963 A | 3/1993 | Parins |
| 5,197,964 A | 3/1993 | Parins |
| 5,318,525 A | 6/1994 | West et al. |
| 5,324,255 A | 6/1994 | Passafaro et al. |
| 5,324,284 A | 6/1994 | Imran |
| 5,396,887 A | 3/1995 | Imran |
| 5,397,304 A | 3/1995 | Truckai |
| 5,400,783 A | 3/1995 | Pomeranz et al. |
| 5,427,119 A | 6/1995 | Swartz et al. |
| 5,429,596 A | 7/1995 | Arias et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,545,195 A | 8/1996 | Lennox et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,693,044 A * | 12/1997 | Cosmescu ............ A61B 18/042 604/35 |
| 5,697,882 A | 12/1997 | Eggers et al. |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,056,744 A | 5/2000 | Edwards |
| 6,056,745 A | 5/2000 | Panescu et al. |
| 6,056,746 A | 5/2000 | Goble |
| 6,056,767 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,717 B1 * | 2/2001 | Ouchi ................ A61B 18/1477 604/114 |
| 6,212,426 B1 | 4/2001 | Swanson |
| 6,217,528 B1 | 4/2001 | Koblish et al. |
| 6,217,575 B1 | 4/2001 | DeVore |
| 6,217,576 B1 | 4/2001 | Tu et al. |
| 6,224,592 B1 | 5/2001 | Eggers et al. |
| 6,231,591 B1 | 5/2001 | Desai |
| 6,235,020 B1 | 5/2001 | Cheng et al. |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |

(56) References Cited

U.S. PATENT DOCUMENTS

| | | | |
|---|---|---|---|
| 6,258,087 B1 | 7/2001 | Edwards et al. | |
| 6,264,650 B1 | 7/2001 | Hovda et al. | |
| 6,266,551 B1 | 7/2001 | Osadchy et al. | |
| 6,270,471 B1 | 8/2001 | Hechel et al. | |
| 6,273,886 B1* | 8/2001 | Edwards | A61B 18/12 606/34 |
| 6,283,988 B1 | 9/2001 | Laufer et al. | |
| 6,283,989 B1 | 9/2001 | Laufer et al. | |
| 6,293,943 B1 | 9/2001 | Panescu et al. | |
| 6,299,633 B1 | 10/2001 | Laufer | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,322,559 B1 | 11/2001 | Daulton et al. | |
| 6,328,736 B1 | 12/2001 | Mulier | |
| 6,332,881 B1 | 12/2001 | Carner et al. | |
| 6,358,248 B1 | 3/2002 | Muller | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,371,956 B1 | 4/2002 | Wilson et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,416,509 B1 | 7/2002 | Goble et al. | |
| 6,419,648 B1 | 7/2002 | Vitek et al. | |
| 6,430,426 B2 | 8/2002 | Avitall | |
| 6,440,130 B1 | 8/2002 | Mulier | |
| 6,443,952 B1 | 9/2002 | Mulier | |
| 6,461,314 B1 | 10/2002 | Pant et al. | |
| 6,461,956 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Muller | |
| 6,477,396 B1 | 11/2002 | Mest et al. | |
| 6,484,727 B1 | 11/2002 | Vaska et al. | |
| 6,488,680 B1 | 12/2002 | Francischelli | |
| 6,502,575 B1 | 1/2003 | Jacobs et al. | |
| 6,508,815 B1 | 1/2003 | Strul et al. | |
| 6,514,250 B1 | 2/2003 | Jahns | |
| 6,517,536 B2 | 2/2003 | Hooven et al. | |
| 6,527,767 B2 | 3/2003 | Wang et al. | |
| 6,537,248 B2 | 3/2003 | Muller | |
| 6,537,272 B2 | 3/2003 | Hoey | |
| 6,558,379 B1 | 5/2003 | Batchelor et al. | |
| 6,558,382 B2 | 5/2003 | Jahns | |
| 6,558,385 B1 | 5/2003 | McClurken et al. | |
| 6,575,969 B1 | 6/2003 | Rittman, III et al. | |
| 6,584,360 B2 | 6/2003 | Francischelli | |
| 6,585,732 B2 | 7/2003 | Muller | |
| 6,602,248 B1 | 8/2003 | Sharps et al. | |
| 6,603,988 B2 | 8/2003 | Dowlatshahi | |
| 6,605,084 B2 | 8/2003 | Acker et al. | |
| 6,610,055 B1 | 8/2003 | Swanson et al. | |
| 6,610,060 B2 | 8/2003 | Muller | |
| 6,613,048 B2 | 9/2003 | Muller | |
| 6,635,034 B1 | 10/2003 | Cosmescu | |
| 6,645,199 B1 | 11/2003 | Jenkins et al. | |
| 6,645,202 B1 | 11/2003 | Pless et al. | |
| 6,648,883 B2 | 11/2003 | Francischelli | |
| 6,656,175 B2 | 12/2003 | Francischelli | |
| 6,663,627 B2 | 12/2003 | Francischelli | |
| 6,666,862 B2 | 12/2003 | Jain et al. | |
| 6,679,882 B1 | 1/2004 | Komerup | |
| 6,682,501 B1 | 1/2004 | Nelson | |
| 6,689,131 B2 | 2/2004 | McClurken | |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,766,202 B2 | 7/2004 | Underwood et al. | |
| 6,766,817 B2 | 7/2004 | da Silva | |
| 6,773,433 B2 | 8/2004 | Stewart et al. | |
| 6,776,780 B2 | 8/2004 | Mulier | |
| 6,807,968 B2 | 10/2004 | Francischelli | |
| 6,827,713 B2 | 12/2004 | Beck et al. | |
| 6,827,715 B2 | 12/2004 | Francischelli | |
| 6,832,996 B2 | 12/2004 | Woloszko et al. | |
| 6,849,073 B2 | 2/2005 | Hoey | |
| 6,858,028 B2 | 2/2005 | Mulier | |
| 6,881,213 B2 | 4/2005 | Ryan et al. | |
| 6,887,238 B2 | 5/2005 | Jahns | |
| 6,899,711 B2 | 5/2005 | Stewart et al. | |
| 6,911,019 B2 | 6/2005 | Mulier | |
| 6,915,806 B2 | 7/2005 | Pacek et al. | |
| 6,916,318 B2 | 7/2005 | Francischelli | |
| 6,942,661 B2 | 9/2005 | Swanson | |
| 6,949,097 B2 | 9/2005 | Stewart et al. | |
| 6,949,098 B2 | 9/2005 | Mulier | |
| 6,953,461 B2 | 10/2005 | McClurken et al. | |
| 6,960,205 B2 | 11/2005 | Jahns | |
| 6,962,589 B2 | 11/2005 | Mulier | |
| 7,066,586 B2 | 6/2006 | da Silva | |
| 7,156,843 B2 | 1/2007 | Skarda | |
| 7,156,845 B2 | 1/2007 | Mulier et al. | |
| 7,166,106 B2 | 1/2007 | Bartel et al. | |
| 7,232,440 B2 | 6/2007 | Dumbauld et al. | |
| 7,247,155 B2 | 7/2007 | Hoey et al. | |
| 7,309,325 B2 | 12/2007 | Mulier et al. | |
| 7,322,974 B2 | 1/2008 | Swoyer et al. | |
| 7,364,579 B2 | 4/2008 | Mulier et al. | |
| 7,651,494 B2 | 1/2010 | McClurken et al. | |
| 7,935,109 B2 | 5/2011 | Cosmescu | |
| 7,972,330 B2 | 7/2011 | Alejandro et al. | |
| 7,976,544 B2 | 7/2011 | McClurken et al. | |
| 8,083,736 B2 | 12/2011 | McClurken et al. | |
| 8,216,233 B2 | 7/2012 | McClurken | |
| 8,323,276 B2 | 12/2012 | Palanker et al. | |
| 8,323,279 B2 | 12/2012 | Dahla et al. | |
| 8,348,946 B2 | 1/2013 | McClurken | |
| 8,361,068 B2 | 1/2013 | McClurken | |
| 8,506,564 B2 | 8/2013 | Long et al. | |
| 8,753,312 B2 | 6/2014 | Bowe et al. | |
| 8,808,287 B2 | 8/2014 | Heard et al. | |
| 8,882,756 B2 | 11/2014 | Greeley et al. | |
| 8,979,842 B2 | 3/2015 | McNall, III et al. | |
| 9,381,061 B2 | 7/2016 | McClurken et al. | |
| 9,445,858 B2 | 9/2016 | Conley et al. | |
| 9,486,283 B2 | 11/2016 | Greeley et al. | |
| 2001/0051802 A1 | 12/2001 | Woloszko et al. | |
| 2002/2258938 | 5/2002 | Cosmescu | |
| 2003/0014050 A1 | 1/2003 | Sharkey et al. | |
| 2003/0032954 A1 | 2/2003 | Carranza et al. | |
| 2003/0045872 A1 | 3/2003 | Jacobs | |
| 2003/0073993 A1 | 4/2003 | Ciarrocca | |
| 2003/0144656 A1 | 7/2003 | Ocel | |
| 2003/0191462 A1 | 10/2003 | Jacobs | |
| 2003/0204185 A1 | 10/2003 | Sherman et al. | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0024395 A1 | 2/2004 | Ellman et al. | |
| 2004/0044340 A1 | 3/2004 | Francischelli | |
| 2004/0049179 A1 | 3/2004 | Francischelli | |
| 2004/0049183 A1* | 3/2004 | Ellman | A61B 18/1485 606/45 |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0111136 A1 | 6/2004 | Sharkey et al. | |
| 2004/0111137 A1 | 6/2004 | Sharkey et al. | |
| 2004/0116923 A1 | 6/2004 | Desinger | |
| 2004/0138621 A1 | 7/2004 | Jahns | |

(56) References Cited

U.S. PATENT DOCUMENTS

| | | |
|---|---|---|
| 2004/0138656 A1 | 7/2004 | Francischelli |
| 2004/0143260 A1 | 7/2004 | Francischelli |
| 2004/0147828 A1 | 7/2004 | Gibson |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2005/0267467 A1 | 12/2005 | Paul et al. |
| 2006/0009756 A1 | 1/2006 | Francischelli |
| 2006/0009759 A1 | 1/2006 | Christian |
| 2006/0064085 A1 | 3/2006 | Schechter et al. |
| 2007/0049920 A1 | 3/2007 | McClurken et al. |
| 2007/0093808 A1 | 4/2007 | Mulier et al. |
| 2007/0112343 A1 | 5/2007 | Mische et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0234674 A1 | 9/2008 | McClurken et al. |
| 2009/0069802 A1* | 3/2009 | Garito ............ A61B 18/14 606/45 |
| 2009/0209975 A1 | 8/2009 | Milijasevic et al. |
| 2009/0222001 A1 | 9/2009 | Greeley et al. |
| 2009/0264879 A1 | 10/2009 | McClurken et al. |
| 2010/0099949 A1* | 4/2010 | Tilson ............ A61B 1/31 600/116 |
| 2010/0100095 A1 | 4/2010 | McClurken et al. |
| 2011/0028965 A1 | 2/2011 | McClurken et al. |
| 2012/0004657 A1 | 1/2012 | Conley et al. |
| 2012/0010149 A1 | 4/2012 | McClurken et al. |
| 2012/0116397 A1 | 5/2012 | Rencher et al. |
| 2012/0191084 A1 | 7/2012 | Davison et al. |
| 2012/0245577 A1 | 9/2012 | Mihalik et al. |
| 2014/0039492 A1 | 2/2014 | Long |
| 2014/0039493 A1 | 2/2014 | Conley et al. |
| 2014/0188105 A1 | 7/2014 | Conley et al. |
| 2014/0257277 A1 | 9/2014 | Woloszko et al. |
| 2015/0320490 A1 | 11/2015 | Conley et al. |

* cited by examiner

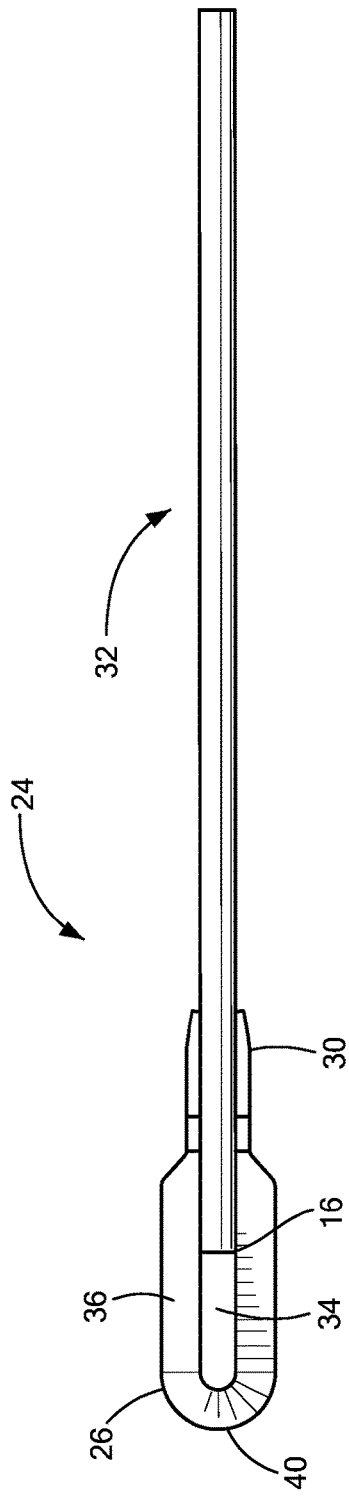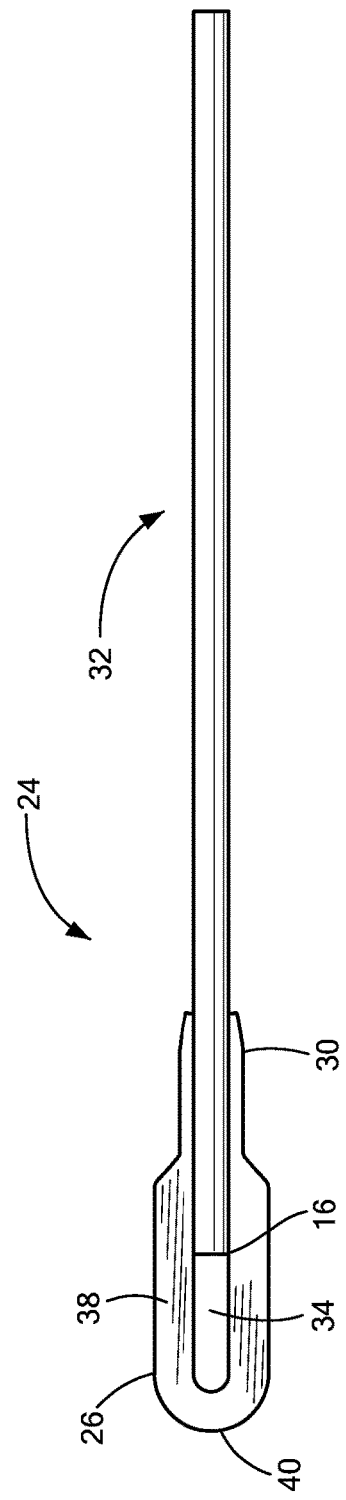
FIG. 4a
FIG. 4b

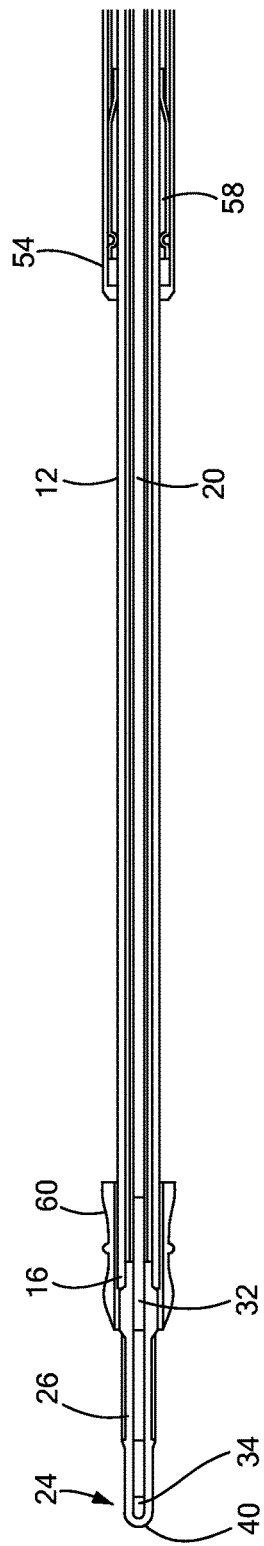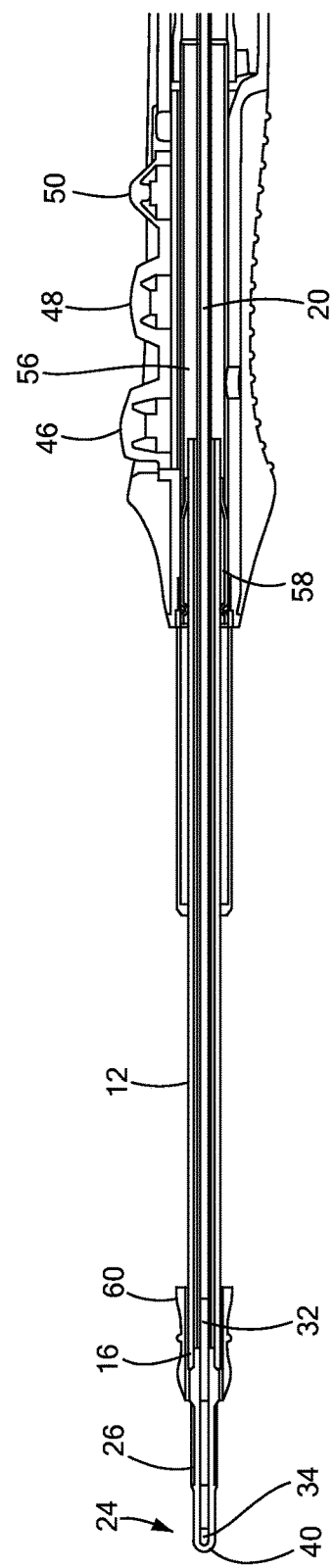

TELESCOPING DEVICE WITH SALINE IRRIGATION LINE

CROSS-REFERENCE TO RELATED APPLICATION

This application is related to and claims priority to U.S. Provisional Patent Application Ser. No. 62/073,705, filed Oct. 31, 2014, entitled COMBINATION PEAK PLASMA AND TRANSCOLLATION TIP, the entirety of which is incorporated herein by reference.

STATEMENT REGARDING FEDERALLY SPONSORED RESEARCH OR DEVELOPMENT n/a

FIELD OF THE INVENTION

The present invention relates to electrosurgical devices, and more particularly, a telescoping electrosurgical device and system with irrigation.

BACKGROUND OF THE INVENTION

Electrosurgical devices are electrically powered medical devices configured to cut, coagulate, desiccate, or fulgurate tissue. Such devices typically employ radio frequency electrical current to heat the target tissue region to effectuate a desired result. One such electrosurgical device uses an electrode to deliver monopolar radiofrequency current to the target tissue to cut and coagulate the tissue to reduce blood and to seal the surgical site.

Both cutting and coagulation modalities transfer a substantial amount of heat to the target tissue, which may result in smoke, tissue charring, the electrode sticking to the tissue, and collateral tissue being destroyed, which may increase surgical times and delay patient healing. Thus, coagulating tissue with a conductive fluid, such as saline, has been devised to rapidly seal tissue during surgery while minimizing charring, smoke, and sticking associated with sealing tissue. However, such surgical devices that provide for the sealing of tissue with saline, do not also cut tissue and a second electrosurgical device is needed to cut the tissue. This is so because the cutting of tissue typically employs a narrow blade delivering radiofrequency energy operating on a long duty cycle, while the coagulation of tissue with saline typically employs a large area electrode operating on a short duty cycle.

Moreover, while telescoping electrosurgical device exists to provide the surgeon with better reach and maneuverability when accessing tissue to be treated, such devices do not provide the ability to irrigate tissue with a fluid during the electrosurgical treatment. The difficulty in providing fluid lies in the fact that extending and retracting the shaft portion of the device may cause compression of the fluid delivery tube, which may result in kinking, leaks, or other malfunctions that prevent integrated irrigation from being utilizes in such electrosurgical devices.

SUMMARY OF THE INVENTION

The present invention advantageously provides for an electrosurgical device, comprising a first shaft defining a proximal end, a distal end, and a lumen there through. A fluid delivery tube is disposed within the lumen, the fluid delivery tube defining a proximal end a distal end. The proximal end of the fluid delivery tube is affixed to the proximal end of the first shaft. An electrically conductive treatment element is in electrical communication with and coupled to the distal end of the first shaft, the electrically conductive treatment element includes a conductive fluid conduit in fluid communication with and affixed within a portion of the fluid delivery tube. A second shaft is in electrical communication with the first shaft, the first shaft being slideably disposed within the second shaft and movable from a first position in which the electrically conductive treatment element is proximate to the distal end of the second shaft to a second position in which the electrically conductive treatment element is advanced a distance away from the distal end of the second shaft.

In another embodiment, an electrosurgical system includes a first shaft defining a proximal end, a distal end, and a lumen there through. A fluid delivery tube is disposed within the lumen, the fluid delivery tube defining a proximal end a distal end. The proximal end of the fluid delivery tube is affixed to the proximal end of the first shaft. An electrically conductive treatment element in electrical communication with and coupled to the distal end of the first shaft is included, the electrically conductive treatment element includes a conductive fluid conduit in fluid communication with and affixed within a portion of the fluid delivery tube. A handle is included, the first shaft being slideably disposed within the handle, the fluid delivery tube maintaining fluid communication with the conductive fluid conduit when the first shaft slides within the handle. A radiofrequency generator in electrical communication with the electrically conductive treatment element is included, the radiofrequency generator including a pump in fluid communication with fluid source, the pump being in fluid communication with the fluid delivery tube. A vacuum source in fluid communication with the lumen may optionally be included, the vacuum source being configured to aspirate fluid expelled from the conductive fluid conduit.

In yet another embodiment, the electrosurgical device includes a conductive first shaft defining a proximal end, a distal end, and a lumen there through. A fluid delivery tube disposed within the lumen is included, the fluid delivery tube defining a proximal end a distal end. The proximal end of the fluid delivery tube is affixed to the proximal end of the first shaft. An electrically conductive treatment element in electrical communication with and coupled to the distal end of the first shaft is included, the electrically conductive treatment element includes a conductive fluid conduit in fluid communication with and affixed within a portion of the fluid delivery tube, the conductive fluid conduit in electrical communication with the first shaft; an electrode defining a sharp, the electrode being configured to cut tissue with radiofrequency energy; and a port disposed distal to the distal end of the conductive fluid conduit, the port configured to expel conductive fluid from the conductive fluid conduit, the electrode surrounding at least a portion of the port. A second shaft in electrical communication with the first shaft is included, the first shaft being slideably disposed within the second shaft and movable from a first position in which the electrically conductive treatment element is proximate to the distal end of the second shaft to a second position in which the electrically conductive treatment element is advanced a distance away from the distal end of the second shaft while fluid communication is maintained between the fluid delivery tube and the conductive fluid conduit. A handle is included, the proximal ends of the first shaft and the second shaft being disposed within the handle.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 4A is a top view of the treatment portion of the electrosurgical device shown in FIG. 1;

FIG. 4B is a bottom view of the treatment portion shown in FIG. 4A

FIG. 6 is a side cross-sectional view of the electrosurgical device shown in FIG. 1 showing the device in a fully extended position;

FIG. 7 is a side cross-sectional view of the electrosurgical device shown in FIG. 1 showing the device in a partially extended position.

DETAILED DESCRIPTION OF THE INVENTION

As used here, relational terms, such as "first" and "second," "top" and "bottom," "front and rear," and the like, may be used solely to distinguish one entity or element from another entity or element without necessarily requiring or implying any physical or logical relationship or order between such entities or elements.

Figure 1:
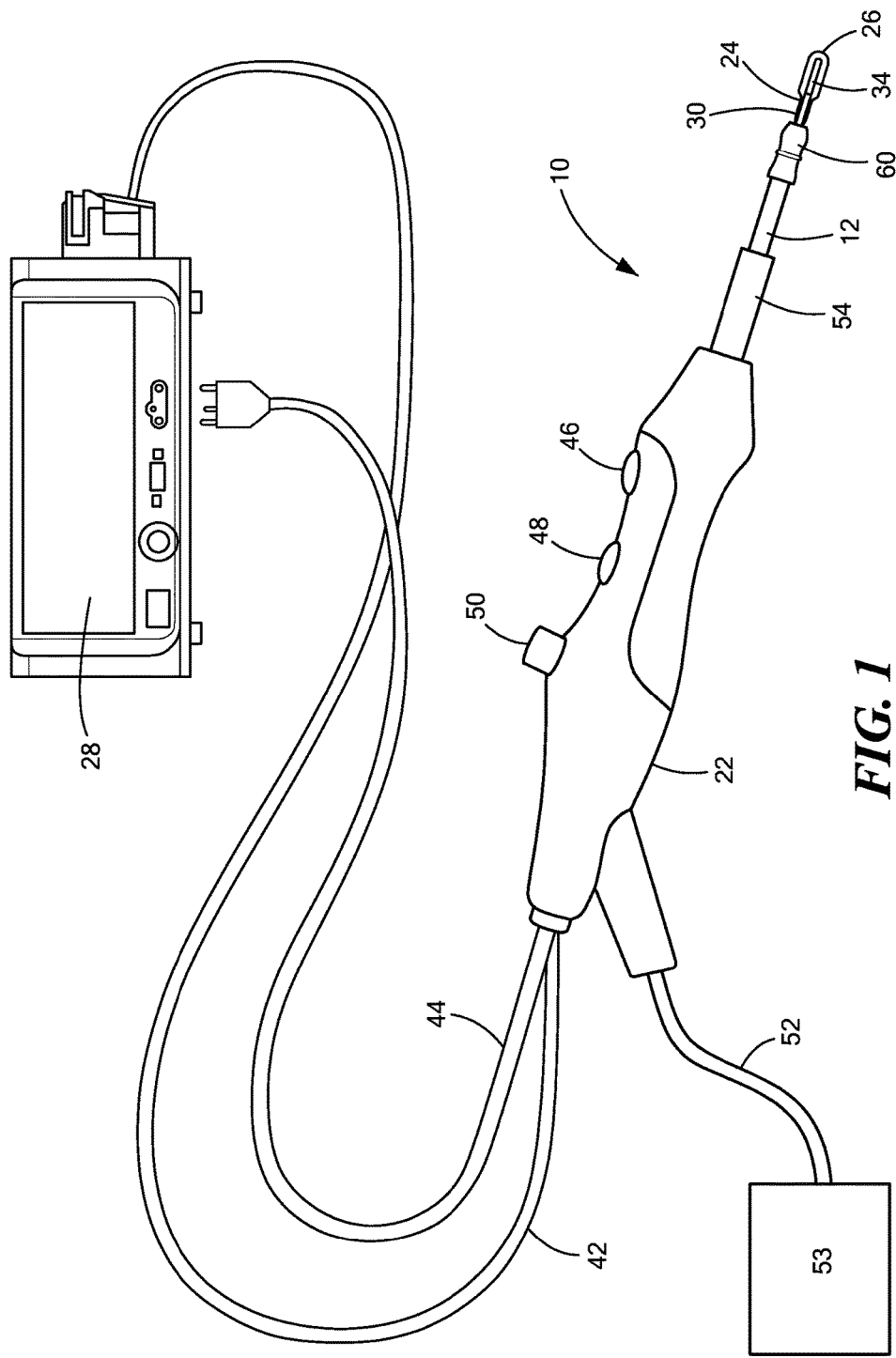
FIG. 1 is a front perspective view of an electrosurgical device and electrosurgical generator constructed in accordance with the principles of the present application.
Figure 2:
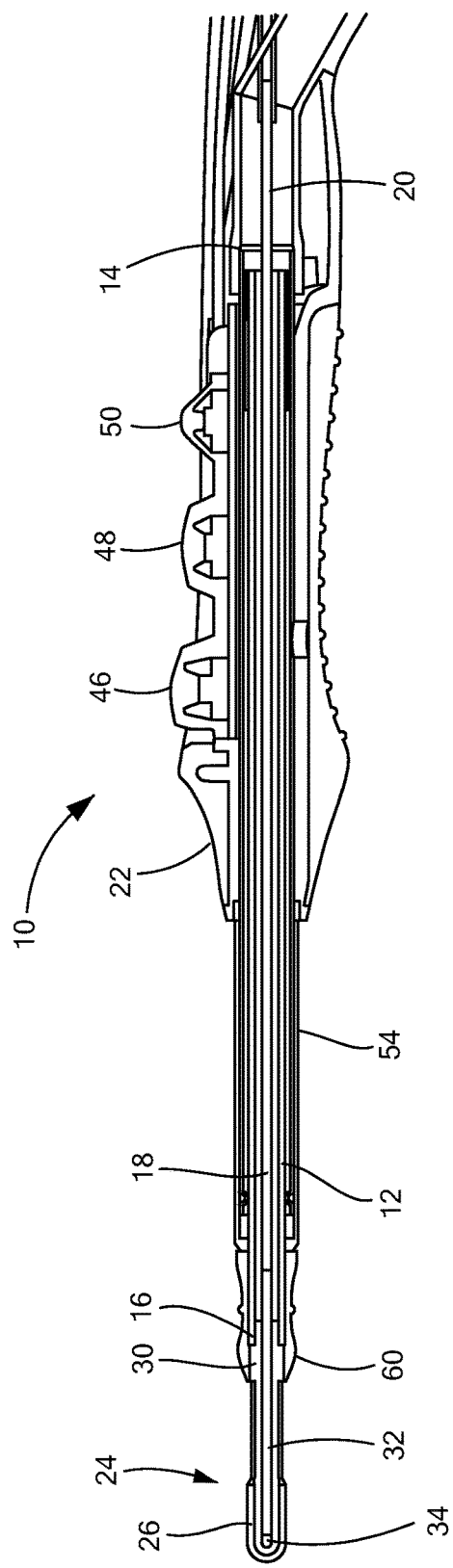
FIG. 2 is a side cross-sectional view of the electrosurgical device shown in FIG. 1 showing the device in a fully retracted position.
Figure 3:
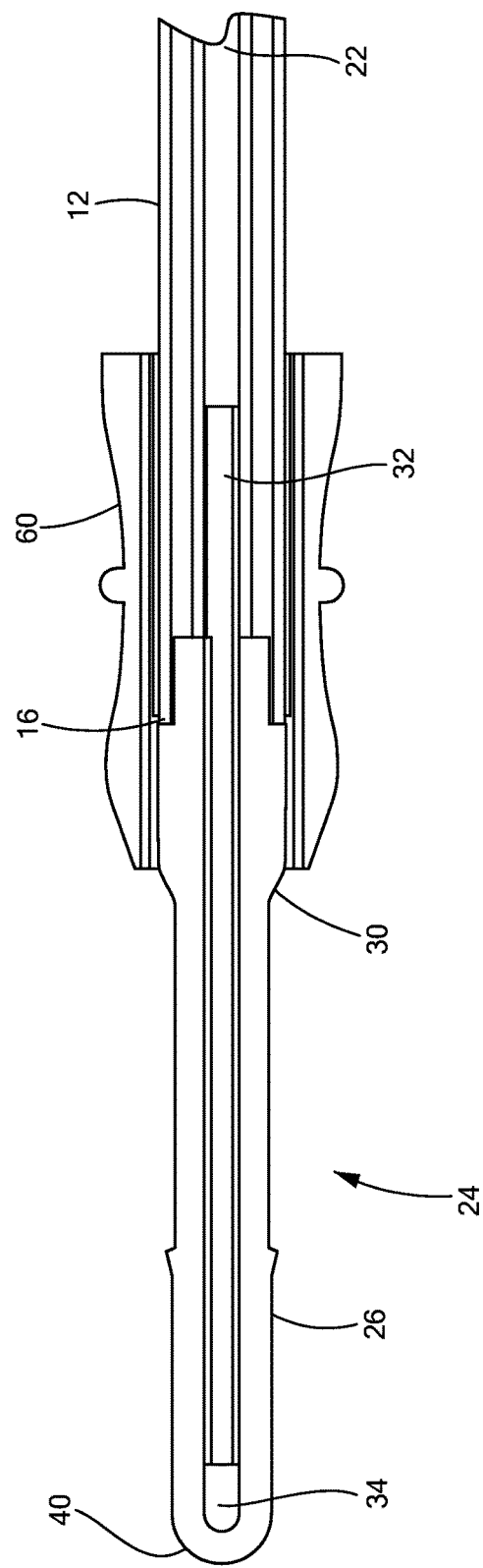
FIG. 3 is a side cross-section view of the distal end of the electrosurgical device shown in FIG. 1.

Now referring to the drawings in which like reference designators refer to like elements, there is shown in FIGS. 1-3, an exemplary electrosurgical device, and its related components, constructed in accordance with the principles of the present application and designated generally as "10." The device 10 may include a first shaft 12 having a proximal end 14 and a distal end 16. The first shaft 12 may be composed of a conductive material, for example, a metal or a metal alloy such as stainless steel, and may be rigid or malleable. The first shaft 12 may further be composed of a non-conductive material, such as polyurethane including a conductor such a wire extending along or within the first shaft 12 from the proximal end 14 to the distal end 16. The surface of the outer diameter of the first shaft 12 may be electrically insulated with, for example, heat shrink that is slid over the exterior surface of the first shaft 12.

The first shaft 12 may define a lumen 18 there through sized to receive a non-conductive fluid delivery tube 20 for transporting a conductive fluid, for example saline, to a target treatment region. In one embodiment, the fluid delivery tube 20 extends within the lumen 18 from the proximal end 14 to the distal end 16 and is co-axial with the first shaft 12. The proximal end 14 of the first shaft 12 is movably and telescopingly coupled to a handle 22 as discussed in more detail below. The handle 22 may include features for activating the various treatment modalities of the device 10 discussed in more detail below. The distal end 16 may include a treatment element 24 extending therefrom configured to deliver at least one of: monopolar energy configured to generate plasma and resect tissue in the target tissue region, referred to herein as CUT mode; monopolar energy configured to coagulated the target tissue region, referred to herein as COAG mode; and monopolar energy combined with saline delivery configured to provide hemostasis to the target tissue region and surrounding tissue, referred to herein as transcollation, or TRANS mode.

The treatment element 24 may include an electrode 26 in electrical communication with a radiofrequency generator 28 configured to transmit radiofrequency energy at a predetermined voltage, frequency, and duty cycle determined by the generator 28 through the target tissue region and toward a patient return electrode (not shown) positioned on or proximate to the patient. For example, the patient return electrode, or ground electrode, may be positioned on the skin of the patient during a procedure such that current may flow from the electrode 26 to the patient return electrode. Generators, pumps and electrical signals suitable for use with the present invention include those described in U.S. Pat. Nos. 7,959,626 and 9,018,983 and Published U.S. Pat. Application Nos. 2006-0149225, 2008-0015562, 2011-0178515 and 2014-0002142, the entire contents of each of which are herein incorporated by reference.

The treatment element 24 may further be in fluid communication with a conductive fluid source, such as saline, either disposed within the generator 28 or independent of and remote from the generator, and whose flow initiation, rate, and termination is controlled by the generator 28 in communication with a pump. In one configuration, the treatment element 24 is welded or otherwise permanently affixed to the distal end 16 of the first shaft 12 to create an electrical connection between the first shaft 12 and the treatment element 24. In other configurations, the treatment element 24 may be modular such that it is releasably affixable to the distal end 16 of the first shaft 12. In particular, treatment elements 24 of various sizes and configurations may be engageable with the distal end 16 of the first shaft 12, for example, through a mechanical interference fit, bayonetted connection, friction fit, and the like. The treatment element 24 may include a necked portion 30 sized engage or otherwise be received and welded within or to the first shaft 12, such that the treatment element 24 may be in fluid communication with the fluid deliver tube 20 and the fluid source, and such that an electrical connection is created between the necked portion 30 and the first shaft 12. In particular, extending proximally from the necked portion 30 is a conductive hypotube 32 fit within the lumen of the fluid delivery tube 20. The hypotube 32 may define a smaller diameter to that of the fluid delivery tube 20 and be composed of, for example, stainless steel. The hypotube 32 may be in electrical communication with the first shaft 12 such that fluid exited the flow delivery tube 20 into the hypotube 32 may be energized by radio frequency energy transmitted by the generator 28.

Referring now to FIGS. 4a-4b, the electrode 26 may define the same, wider, or smaller diameter to that of diameter of the first shaft 12. The electrode 26 may define a circular, triangular, ovular, or curved cross-section, or any shape, in which the electrode 26 defines a slot or port 34 configured to enable to the perfusion of a conductive fluid there through during TRANS mode. In the configuration shown in FIGS. 4a-4b, the electrode 26 defines a closed looped with the hypotube 32 such that the slot 34 extends from a position proximal to the distal end of the electrode 26 to a position distal to the proximal end of the electrode 26. The size of slot 34 may vary and in one configuration forms a needle eye with the electrode 26 surrounding the slot 34 to provide for a slower perfusion by capillary action of fluid out through the slot 34 and in other configurations the slot if larger to provide for a larger volume of fluid perfused through the slot 34. For example, as shown in FIGS. 2a and 2b, the lumen 18 of the hypotube 32 may extend into and be in fluid communication with the slot 34, such that fluid egressing the distal end of the hypotube 32 exits the device 10 through the slot 34. In other configurations, the slot 34 may be a pin hole or a plurality of slots 34 may be included around or within the electrode 26 such that the electrode 26 may be porous. The size of the slot 34 may range from approximately 0.05 inches to 0.015 inches in length and may range in width from 0.025 inches to 0.04 inches. In yet another configuration, instead of a slot 34, the treatment element 24 may define a cavity sized to retain and heat a volume of a saline within the cavity as it perfused from the lumen of the hypotube 32. In particular, a pump independent of or associated with the generator 28 may be configured to inject a bolus or continuous flow of saline into the fluid delivery tube 20 of sufficient volume to fill the cavity. When the user actuates the device 10 to deliver saline to the cavity, the electrode 26 may be sequentially or simultaneously activated by actuation of the device 10.

Figure 5:
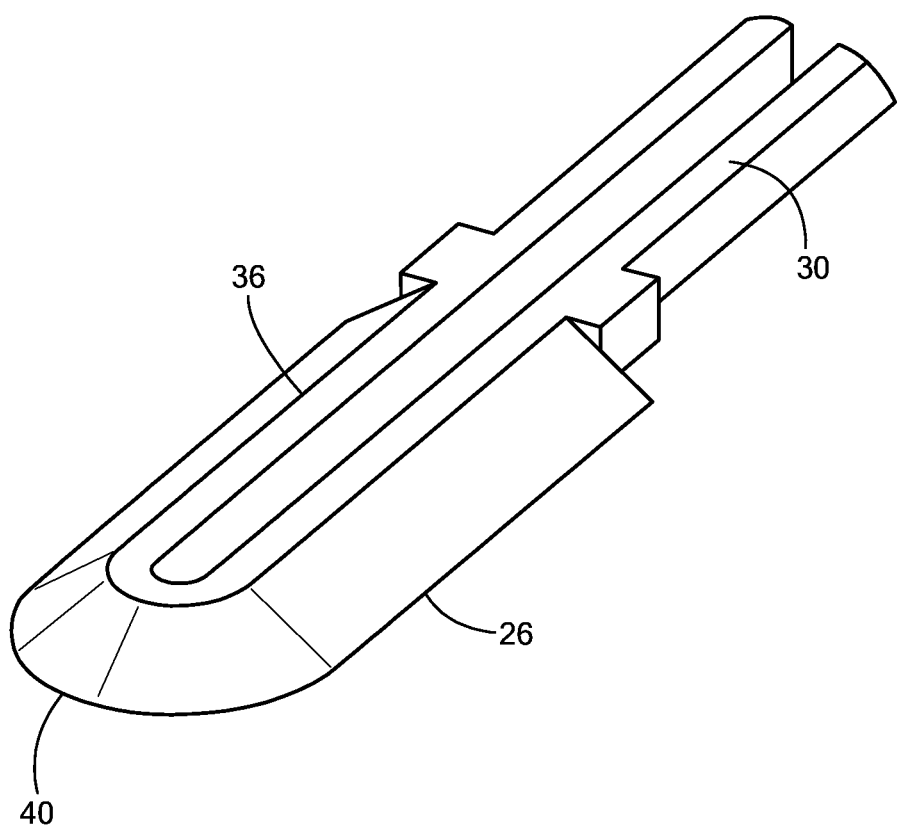
FIG. 5 is a top perspective view of the treatment portion shown in FIGS. 4A and 4B with the hypotube removed.
Figure 8:
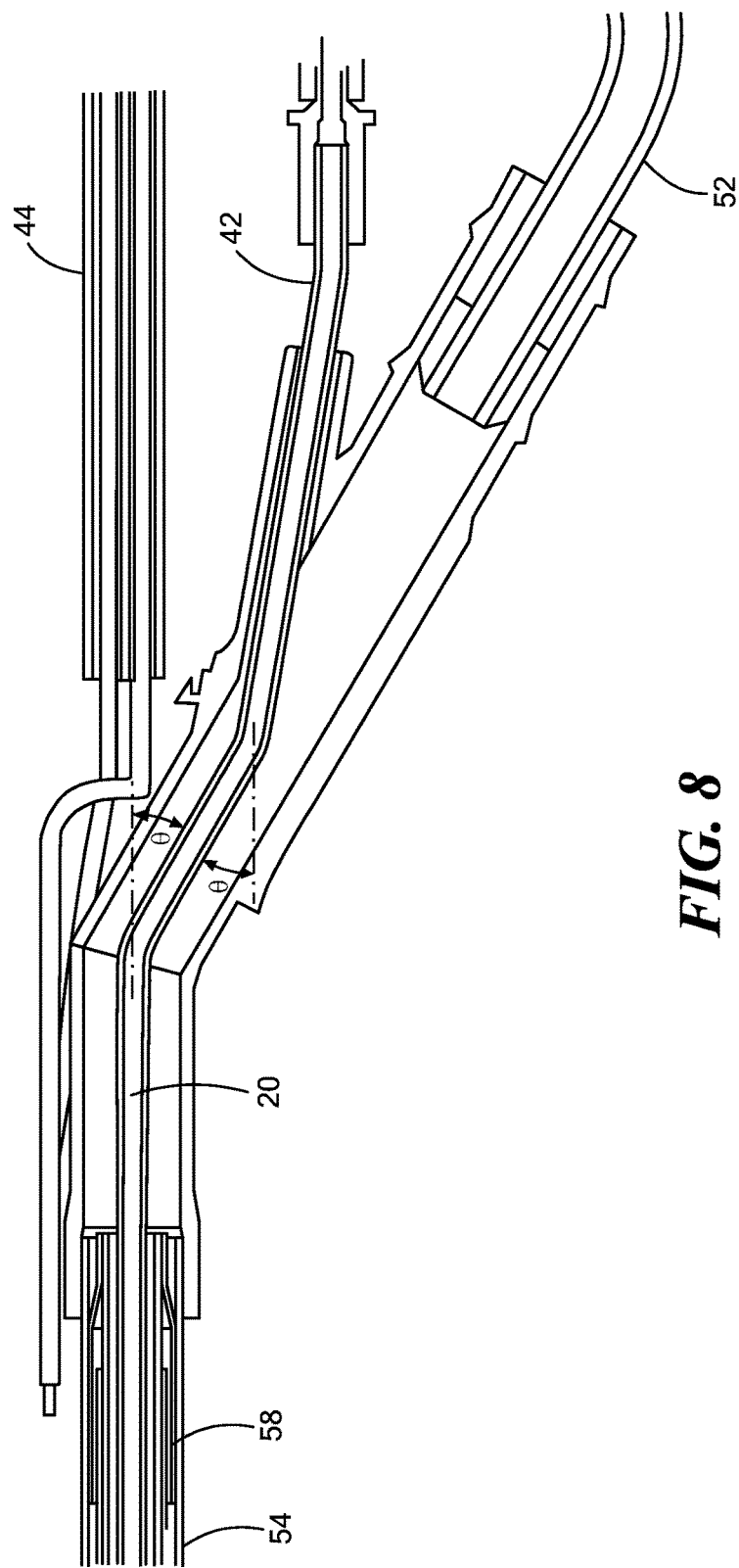
FIG. 8 is a side cross-sectional view of the proximal portion of the electrosurgical device shown in FIG. 1 with the handle removed.

Referring now to FIG. 5 which shows the hypotube 32 removed, the electrode 26 may define a blunt, sharp, or sloped surface extending at an oblique angle around the perimeter of the electrode 26, and may be rigid or malleable. For example, a substantially planar top surface 36 of the electrode 26 may define a beveled edge around its perimeter with the beveled edge extending from the substantially planar top surface 36. A bottom surface 38 of the electrode 26 may be substantially planar such that it may readily glide over the tissue to be treated when saline is disposed between the tissue to be treated and the bottom surface 38 of the electrode 26. In one configuration, the distal end of the electrode 26 may be curved to provide for a larger surface area to spread dispersed saline. In one configuration, the top and/or bottom surfaces of the electrode 26 may be substantially coated with an electrically insulating material, for example, glass. In particular, to increase the current density flowing from the electrode 26 during CUT mode, substantially the entire top and bottom surfaces of the electrode 26 may be coated with glass and an edge 40 of the electrode 26 is uncoated or thinly coated such that an applied voltage leads to a dielectric breakdown on the edge 40 and exposes it. That is, current flows from the uncoated edge 40 of the electrode 26 and not from the coated portion, such that treatment of tissue is effectuated from the edge of the electrode 26 and smoke, charring, sticking, damage and destruction of collateral tissue is minimized. The coating may be uniform around the electrode 26, or may be substantially thinner toward the edge 40 the electrode 26, for example, approximately 20 microns thick, as to avoid cracking, and thicker, for example, approximately 80 microns as it extends toward the center of the electrode 26. The bottom surface 38 of the electrode 26 may be uncoated to decrease the current density when treating tissue in COAG or TRANS mode.

Referring back now to FIG. 1, the handle 22 may include a first umbilical 42 fluidly coupled to a fluid source, such as saline, (not shown) and a second umbilical 44 electrically coupling the first shaft 12 to the radiofrequency generator 28. Both the first umbilical 42 and the second umbilical 44 may be coupled to the generator 28 via separate portions or may combined into a single plug connected to the generator 28. The handle 22 may further include a first actuator 46 configured to operate the device 10 in CUT mode, which applies a maximum voltage in the range of approximately 500V to 1250V, at a duty cycle of approximately 0.2% to 100% (depending on the burst duration, which may range from approximately 7 to 80 microseconds), and at a frequency of approximately 0.4 MHz; a second actuator 48, configured to operate the device 10 in COAG mode, which applies a maximum voltage in the range of approximately 700V to 2600V, at a duty cycle of approximately 6-56% (depending on the burst duration, which may range from approximately 5-40 microseconds), and at a frequency of approximately 0.4 MHz; and a third actuator 50 configured to operate the device 10 in TRANS mode, which applies similar voltages, frequencies, and duty cycles to that of pure CUT mode. Actuation of the third actuator 50 is also configured to initiate the flow of saline at a constant, adjustable, or variable flow rate toward the distal end 16 of the device 10 and out through the slot 34. For example, the generator may be pre-programmed to initiate a flow of fluid at a predetermined rate when the third actuator 50 is actuated. The generator 28 may also be programmed to adjust the flow rate based on the velocity and/or acceleration at which the device 10 is moved across a target tissue region. For example, the device 10 may include an accelerometer (not shown) in the handle 22 configured to measure the velocity and/or acceleration at which the device 10 is moved over the treatment region and increase or decrease the flow based on the measured acceleration or velocity. When the device 10 is set in TRANS mode, the user may move the treatment element 24 over the target region in a painting motion, for example, by pulling the device 10 across the target tissue region such that as fluid is dispersed out through slot 34 and contacts the edge 40. In one configuration, when the device is set to TRANS mode, the insulated conductive wire may apply a voltage to the electrode 26 such that the hypotube, though the saline may be flowing, does not boil the saline with the hypotube 32. The energy transmitted by the electrode 26 is conducted by the conductive fluid such that the monopolar energy is directed toward the target tissue region and the surrounding tissue. If the user accelerates movement of the device 10, the flow rate of saline toward the treatment element 24 may increase to provide for increased lubrication, whereas a decreased flow rate may be provided for by the generator if the user decelerates movement of the device 10.

Continuing to refer to FIG. 1, the first shaft 12 may further include an exhaust lumen 52 in communication with a vacuum source 53 in a remote device, the exhaust lumen 52 being disposed between the outer diameter of the fluid delivery tube 20 and the inner diameter of the first shaft 12. The vacuum source is configured to suction the conductive fluid from the target tissue region. For example, after treating tissue in TRANS mode it may be desirable to switch modes to COAG or CUT to effectuate further treatment. The vacuum source 53 may automatically begin to suction saline from the tissue region for a predetermined period of time, or alternatively, may suction by saline by actuation of the first actuator 46 or the second actuator 48 following treatment in TRANS mode. Alternatively, the generator 28 may provide for a delay between TRANS mode and COAG or CUT mode to provide for saline to be diffused or boiled from the surface following TRANS treatment. For example, the generator 28 may provide that for a predetermined period of time, for example, approximately two to ten seconds following the termination of treatment in TRANS mode, that CUT or COAG mode cannot be initiated to provide for the proper function of the device 10 in a dry (no saline) COAG mode or dry CUT mode. The device 10 may further include a smoke suction tube (not shown) at the distal end of the first shaft 12 configured to vacuum any smoke generated from the resection of tissue. The smoke suction tube may be in communication with a vacuum and may be co-axial around or within the first shaft 12 or may be a separate tube within the device 10.

Referring now to FIGS. 2 and 6-7, the device 10 may further include one or more mechanical features to provide for particular treatments for particular tissue regions. For example, the first shaft 12 may be telescopingly coupled to the handle 22 to allow for the extension and retraction of the first shaft 12 into and out of a portion of the handle 22. In particular, the first shaft 12 may be slideable disposed within a second shaft 54, which surrounds and is co-axially disposed about at least a portion of the first shaft 12. The first shaft 54 may be composed of the same or similar material of the first shaft 12, for example, stainless steel or any conductive metal or metal allot, and may be substantially rigid in construction. The second shaft 54 may similar be disposed within a portion of the handle 22 and may form an electrical connection with the actuators 46, 48, and 50. For example, one or more conductors may conduct a radiofrequency signal from the generator 28 in respond to the actuation of the actuators 46, 48, and 50 which in turns transmit a signal to the second shaft 54. In an exemplary configuration, the second shaft 54 extends a distance away from the distal end of the handle 22 and includes heat shrink around its exterior to provide insulation for the portion that extends beyond the distal end of the handle 22. The second shaft 54 may terminate at a position proximal to the distal of the first shaft 12 and is sized such that the first shaft 12 nests within a lumen 56 of the second shaft 42.

Disposed between the inner diameter of the second shaft 54 and the outer diameter of the first shaft 12 may be an electrically conductive sliding element 58. The sliding element 58 may be circumferentially disposed about and affixed to the outer diameter of the first shaft 12. The sliding element 58 is configured to allow the extension and retraction of the first shaft 12 within the second shaft 54. The sliding element 58 may be composed of a flexible metal or metal alloy, for example, beryllium copper and may conduct a radiofrequency signal from the second shaft 54 through the sliding element 58 to the first shaft 12 where it is further conducted to the treatment element 24.

Affixed proximal to the distal end of the first shaft 12 may be a gripping element 60. The gripping element 60 is configured such that a user can pinch the gripping element 60 and push or pull on the gripping element 60 to retract or extend to the first shaft 12, respectively. The gripping element 60 may be affixed along any portion of the first shaft 12 and may composed of any electrically insulating material. In an exemplary configuration, the gripping element 60 is disposed on opposite sides of the first shaft 12 and conforms to the users thumb and index fingers.

In an exemplary configuration, the sliding element 58 maintains electrical contact with second shaft 54 as it slides within the second shaft 54. In particular, when the device 10 is in a fully retracted position (FIG. 2), the proximal ends of the first shaft 12, second shaft 54, and the sliding element are substantially co-terminus. As the first shaft 12 slides distally within the lumen 56 of the second shaft 54, the sliding element 58 slides with the first shaft 12 to a desired longitudinal position within the second shaft 54. Sufficient friction may be present between the inner wall of the second shaft 54 and the sliding element 58 such that the first shaft 12 may remain in a first position within the second shaft 54 until pulled or pushed to a second position within shaft 54. In a fully extended positioned (FIG. 6), the distal end of the sliding element 58 is substantially co-terminus with the distal end of the second shaft 54. To prevent the sliding element 58 from being advanced out of the second shaft 54 and to provide for a smooth transition between the fully extended and retracted positions, the sliding element 58 may have a tapered distal end and the second shaft 54 may define one or more prongs or may be narrowed such that the sliding element 58 may not advance out through the distal end of the second shaft 54.

Now referring to FIG. 7, when the device 10 is pushed toward the fully retracted position and pulled from the fully retracted position, the fluid delivery tube 20 may slide within a lumen within the handle 22 defined at the proximal end of the handle 22 distal to the first umbilical 42. The fluid delivery tube 20 may slide back and forth within the handle 22 as the first shaft 12 is advanced and retracted without kinking within the handle 22. This is due, in part, to the stiffness of the fluid delivery tube 20, which is sufficiently stiff to avoid kinking when the fluid delivery tube 20 is pushed. Moreover, the handle 22 may include one or more oblique angles "θ", for example, between 15 and 45 degrees that provide a soft angle for the fluid deliver tube 20 to bend within to prevent kinking. Because the distal end of the fluid delivery tube 20 is affixed to the treatment element 24, which is affixed to the distal end of the first shaft 12, the fluid delivery tube 20 moves with the first shaft 12 as it is extended and retracted while continuously maintaining fluid communication with the treatment tip 24 and the hypotube 32.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An electrosurgical device, comprising:
   a first shaft defining a proximal end, a distal end, and a lumen there through;
   a fluid delivery tube disposed within the lumen, the fluid delivery tube defining a proximal end a distal end, the fluid delivery tube being movable with the first shaft;
   an electrically conductive treatment element in electrical communication with and coupled to the distal end of the first shaft, the electrically conductive treatment element including a conductive fluid conduit in fluid communication with and affixed within a portion of the fluid delivery tube;
   a second shaft in electrical communication with the first shaft, the first shaft being slideably disposed within the second shaft and movable from a first position in which the electrically conductive treatment element is proximate to a distal end of the second shaft to a second position in which the electrically conductive treatment element is advanced a distance away from the distal end of the second shaft; and
   a handle, the proximal end of the first shaft and a proximal end of the second shaft being disposed within the handle, the fluid delivery tube being slideable at an oblique angle within at least a portion of the handle.

2. The device of claim 1, wherein the electrically conductive treatment element includes an electrode having a sharp edge disposed at its distal end, the electrode being configured to cut tissue with monopolar ablation energy.

3. The device of claim 2, wherein the electrically conductive treatment element includes a port proximate to the sharp edge, the port being in fluid communication with the conductive fluid conduit and configured to expel a conductive fluid from the conductive fluid conduit.

4. The device of claim 3, wherein the sharp edge is disposed about the port.

5. The device of claim 3, wherein the port is distal to the distal end of the conductive fluid conduit.

6. The device of claim 1, further including an umbilical disposed within the handle, the umbilical being in fluid communication with the lumen and couplable to a vacuum source configured to aspirate fluid from the lumen.

7. The device of claim 1, further including a slideable element disposed between the first shaft and the second shaft and affixed to the first shaft, the slideable element being moveable from a first position within the handle to a second position distal to the handle.

8. The device of claim 7, wherein the slideable element is conductive, and wherein the second shaft includes a conductor configured to conduct radiofrequency energy from a radiofrequency energy source, and wherein the slideable element transfers the radiofrequency energy from the second shaft to the first shaft.

9. The device of claim 7, wherein the second position is substantially coterminous with the distal end of the second shaft.

10. The device of claim 1, further including a finger grip affixed to an exterior of the first shaft.

11. An electrosurgical system, comprising:
a first shaft defining a proximal end and a distal end, and a lumen there through;
a fluid delivery tube disposed within the lumen, the fluid delivery tube defining a proximal end a distal end and extending from at least the proximal end of the first shaft to proximal the distal end of the first shaft;
an electrically conductive treatment element in electrical communication with and coupled to the distal end of the first shaft, the electrically conductive treatment element including a conductive fluid conduit in fluid communication with and affixed within a portion of the fluid delivery tube;
a handle, the first shaft being slideably disposed within the handle, the fluid delivery tube maintaining fluid communication with the conductive fluid conduit when the fluid delivery tube slides within the handle at an oblique angle; and
a radiofrequency generator in electrical communication with the electrically conductive treatment element, the radiofrequency generator including a pump in fluid communication with a fluid source, the pump being in fluid communication with the fluid delivery tube; and
a vacuum source in fluid communication with the lumen, the vacuum source being configured to aspirate fluid expelled from the conductive fluid conduit.

12. The system of claim 11, further including a second shaft in electrical communication with the first shaft, the first shaft being slideably disposed within the second shaft and movable from a first position in which the electrically conductive treatment element is proximate to a distal end of the second shaft to a second position in which the electrically conductive treatment element is advanced a distance away from the distal end of the second shaft.

13. The device of claim 11, wherein the electrically conductive treatment element includes an electrode having a sharp edge disposed at its distal end, the electrode being configured to cut tissue with monopolar ablation energy.

14. The device of claim 13, wherein the electrically conductive treatment element includes a port proximate to the sharp edge, the port being in fluid communication with the conductive fluid conduit and configured to expel the fluid from the conductive fluid conduit.

15. The device of claim 14, wherein the sharp edge is disposed about the port; and wherein the port is distal to the distal end of the conductive fluid conduit.

16. The device of claim 12, further including a conductive slideable element disposed between the first shaft and the second shaft, the conductive slideable element being moveable from a first position within the handle to a second position distal to the handle.

17. The device of claim 16, wherein the second shaft includes a conductor configured to conduct radiofrequency energy from the radiofrequency generator, and wherein the slideable element is configured to transfer radiofrequency energy from the second shaft to the first shaft.

18. The device of claim 17, wherein the second position is substantially coterminous with the distal end of the second shaft.

19. An electrosurgical device, comprising:
a conductive first shaft defining a proximal end, a distal end, and a lumen there through;
a fluid delivery tube disposed within the lumen, the fluid delivery tube defining a proximal end a distal end, the fluid delivery tube being co-axial with the first shaft;
an electrically conductive treatment element in electrical communication with and coupled to the distal end of the first shaft, the electrically conductive treatment element including:
a conductive fluid conduit in fluid communication with and affixed within a portion of the fluid delivery tube, the conductive fluid conduit in electrical communication with the first shaft;
an electrode defining a sharp edge, the electrode being configured to cut tissue with radiofrequency energy; and
a port disposed distal to the distal end of the conductive fluid conduit, the port configured to expel conductive fluid from the conductive fluid conduit, the electrode surrounding at least a portion of the port;
a second shaft in electrical communication with the first shaft, the first shaft being slideably disposed within the second shaft and movable from a first position in which the electrically conductive treatment element is proximate to a distal end of the second shaft to a second position in which the electrically conductive treatment element is advanced a distance away from the distal end of the second shaft while fluid communication is maintained between the fluid delivery tube and the conductive fluid conduit; and
a handle, the proximal end of the conductive first shaft and a proximal end of the second shaft being disposed within the handle, the fluid delivery tube being slideable at an oblique angle within at least a portion of the handle.

* * * * *